Figure 1:
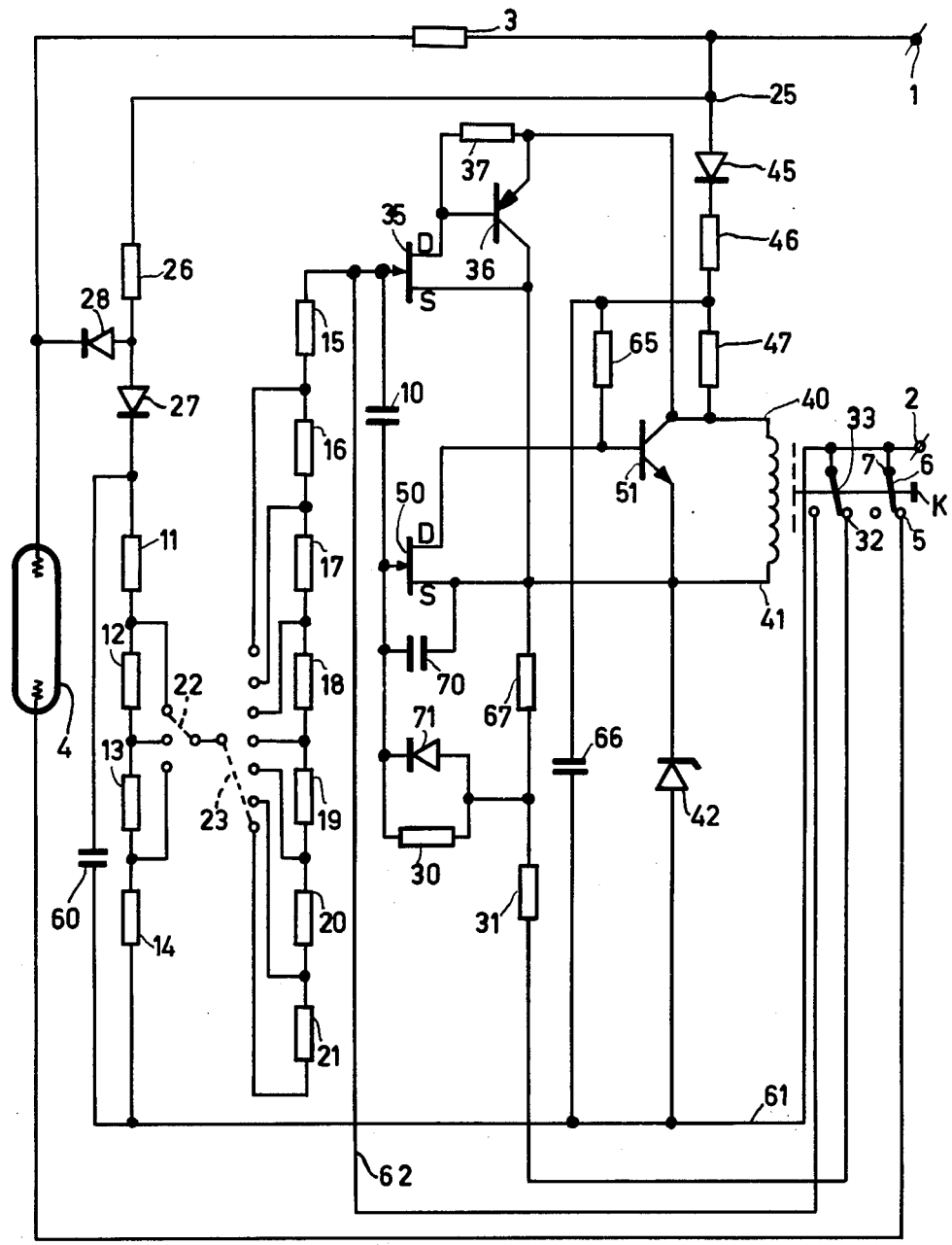

United States Patent [19]

van der Meulen

[11] 4,189,665
[45] Feb. 19, 1980

[54] IRRADIATION APPARATUS

[75] Inventor: Andries van der Meulen, Drachten, Netherlands

[73] Assignee: U.S. Philips Corporation, New York, N.Y.

[21] Appl. No.: 878,825

[22] Filed: Feb. 17, 1978

[30] Foreign Application Priority Data

Mar. 3, 1977 [NL] Netherlands ................. 7702260

[51] Int. Cl.² .......................................... H05B 41/36
[52] U.S. Cl. ................................. 315/360; 307/141.4; 315/119; 315/240; 315/340; 315/362; 361/198
[58] Field of Search .............. 315/119, 227 R, 340, 315/360, 362, 240; 328/7; 307/141.4, 326; 361/197, 200, 198

[56] References Cited

U.S. PATENT DOCUMENTS

| 3,909,659 | 9/1975 | van der Meulen ............. 315/360 X |
| 4,013,922 | 3/1977 | van der Meulen ............. 315/362 |

*Primary Examiner*—Eugene R. La Roche
*Attorney, Agent, or Firm*—Thomas A. Briody; William J. Streeter; Bernard Franzblau

[57] ABSTRACT

The invention relates to a sun lamp provided with a timer circuit that includes a capacitor. As soon as the capacitor reaches a certain charge condition the sun lamp is switched-off.

The sun lamp also comprises a safety circuit responsive to a given level of current through the capacitor, which indicates a defect in the timer circuit 2, to rapidly terminate the irradiation.

15 Claims, 2 Drawing Figures

IRRADIATION APPARATUS

The invention relates to an irradiation apparatus comprising a gas and/or vapour discharge tube and a timer circuit comprising a capacitor. By means of an auxiliary device, the timer circuit serves to reduce, after a desired radiation period, the intensity of the radiation emitted in the radiation direction of the irradiation apparatus. A safety circuit is provided to reduce the intensity of the radiation emitted in the radiation direction in the case of a failing timer circuit.

A prior art irradiation apparatus of the type described is, for example, disclosed in German "Offenlegungsschrift" No. 1,801,982. A drawback of that known irradiation apparatus is that the safety circuit does not start operating until it appears that the timer circuit is unable to reduce the intensity of the radiation in time. This often results in an unwanted additional dose of radiation on the irradiated object, for example a person irradiated with ultraviolet radiation.

It is an object of the invention to obtain a more rapid reduction in the intensity of the radiation in the case of a defective timer circuit.

An irradiation apparatus according to the invention comprises a gas and/or vapour discharge tube and a timer circuit provided with a capacitor. By means of an auxiliary device, the timer circuit serves to reduce, after a desired radiation period, the intensity of the radiation emitted in the radiation direction of the irradiation apparatus, a safety circuit being present to reduce the intensity of the radiation emitted in the radiation direction in the case of a failing timer circuit. The invention is characterized in that the safety circuit includes means to determine during irradiation whether the current through a circuit element in series with the capacitor falls to below a threshold value. The aforesaid means are coupled to the auxiliary device for reducing the intensity of the radiation and said coupling is such that with a capacitor current which is lower than the threshold value the auxiliary device reduces the intensity of the radiation.

An advantage of an irradiation apparatus according to the invention is that a defect in the timer circuit can be rapidly detected and that an automatic response thereto is possible. Too low a capacitor current is detected which might otherwise result in too slow an operation of the timer circuit. In an irradiation apparatus according to the invention the response thereto results in a rapid reduction of the radiation intensity by means of the auxiliary device. So one does not wait until it is apparent that the timer circuit is taking too much time to perform its task. The risk of an overdose of radiation on the object to be irradiated can consequently be small.

It is conceivable that the intensity of the radiation in the radiation direction of the irradiation apparatus can be reduced by, for example, obstructing the beam wholly or partly by a flap or a slide. It is alternatively possible to affect the intensity reduction by subjecting the irradiation apparatus to a swivelling action. As described in the next paragraph, another way to reduce the irradiation is to switch off the energy supply to the discharge tube. All of these techniques effectively reduce the tube irradiation as that term is used herein and in the claims.

In an embodiment of an irradiation apparatus according to the invention, wherein a relay contact which is in series with the discharge tube is included in a supply circuit of the discharge tube, the auxiliary device for reducing the intensity of the radiation is provided with an energizing device of the relay contact in such a way that a capacitor current which is lower than the threshold value opens the relay contact via the energizing device. An advantage of this embodiment is that if the capacitor current is too low, which indicates a defect in the timer circuit, the discharge tube is switched off via the relay contact. The irradiation apparatus can then no longer emit radiation.

The circuit element in series with the capacitor is preferably a meauring resistor. An advantage of this embodiment is that this circuit element can be simple.

It is conceivable that the irradiation by means of the discharge tube starts when the capacitor is in an uncharged condition.

In a further embodiment of an irradiation apparatus according to the invention, wherein the electric charge on the capacitor is varied during the irradiation in one direction only, means are provided to apply to the capacitor, prior to radiation, an initial voltage of such a polarity that the above-mentioned change in the charge is a discharge of the capacitor. An advantage of this embodiment is that, in the case of a defective capacitor, for example, one that is leaking or short-circuited, this defect is detached so that the discharge tube can be switched-off in time.

In an improvement of the last-mentioned embodiment, the means for applying an initial voltage to the capacitor comprise a switch and a zener diode. An advantage of this embodiment is that it is possible to give the capacitor a well-defined initial voltage in a simple manner.

To determine whether the capacitor current falls to below a given threshold value use might, for example, be made of a current transformer having an indicator, for example an auxiliary lamp, in its secondary circuit.

In a further embodiment of an irradiation apparatus according to the invention, the means for detecting whether the capacitor current falls to below the threshold value consists of a first field effect transistor whose control electrode is connected to a junction between the capacitor and the measuring resistor, another electrode of this transistor being connected via a further circuit element to the other side of the measuring resistor.

An advantage of this preferred embodiment is that it is now possible to detect in a simple manner with such a transistor whether the capacitor current falls to below a threshold value.

It might, for example, be possible to switch off the relay contact in series with the discharge tube via a first field effect transistor by means of a photo-coupler.

In a further embodiment of an irradiation apparatus according to the invention, the first field effect transistor is part of a control circuit of a first auxiliary transistor, the main electrode circuit of the auxiliary transistor shunting the energizing winding of the relay which is in series with the discharge tube, the relay contact being a make contact. The term make-contact means a normally open contact, which closes if the relay is energized. An advantage of this embodiment is that releasing the relay can be realized in a simple manner.

In the timer circuit of the irradiation apparatus one might, for example, connect a voltage-sensitive luminous device across the capacitor, which device lights up when the desired radiation time has been reached so that the discharge tube is then switched-off via a light-sensitive component.

The electrode of the capacitor facing away from the measuring resistor may be connected to a control electrode of a second field effect transistor which is part of the timer circuit. Thus it is possible to switch a non-defective timer circuit off in the normal manner via said second field effect transistor.

In a further improvement of the last-mentioned embodiment, the second field effect transistor is part of a control circuit for a second auxiliary transistor, the main electrode circuit of that second auxiliary transistor—just like the main electrode circuit of the first auxiliary transistor—shunting the energizing winding of the relay contact. An advantage of this embodiment is that the same energizing winding of the relay can be used for both the normal switch-off of the irradiation apparatus with a non-defective timer circuit, and for switching-off a defective timer circuit.

Figure 2:
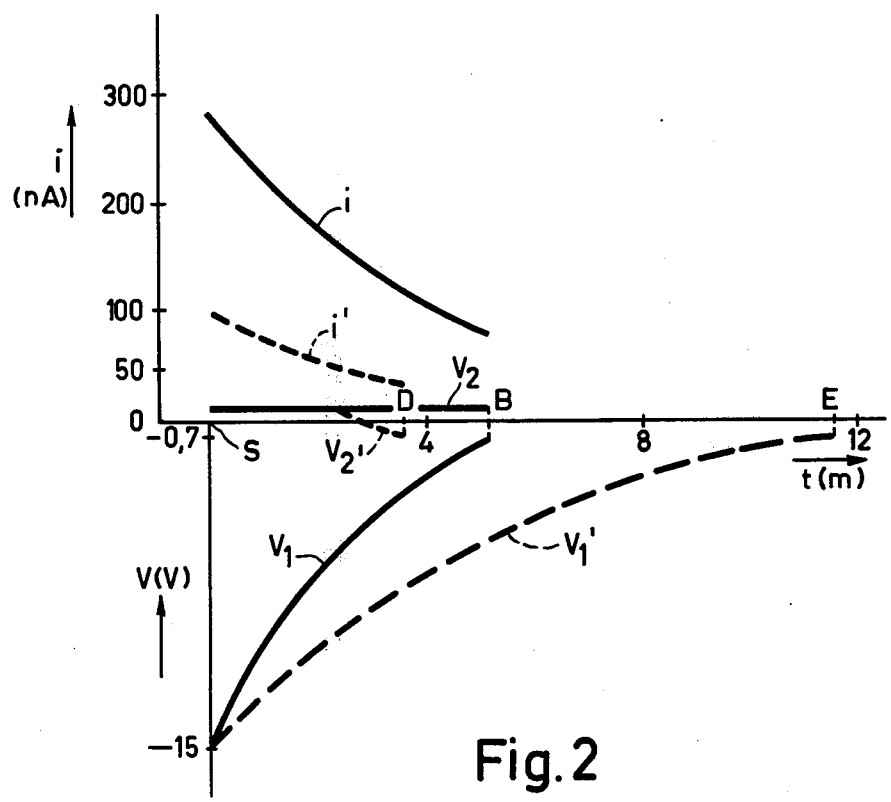

An embodiment of the invention will be further explained with reference to the accompanying drawings, in which:

FIG. 1 shows an electric circuit of an irradiation apparatus according to the invention; in this case a sunlamp; and FIG. 2 is a graph of various capacitor currents and voltages, plotted against time, which can occur in a normal case and in the case of a defect in the circuit of FIG. 1.

In FIG. 1, connecting terminals 1 and 2 are intended for connection to a power supply of approximately 220 V, 50 Hz. Terminal 1 is connected to a resistor 3 which may, for example, be in the form of an infrared radiator. The other side of resistor 3 is connected to an electrode of a high-pressure discharge tube 4. This is a high-pressure mercury vapour discharge tube which emits ultraviolet radiation in the operating condition. A further electrode of the tube 4 is connected to a contact 5 of a switch 6. A contact 7 of this switch 6 is connected to the input terminal 2. The portion of the circuit described so far is referred to as the main circuit.

The main circuit may also be provided with a selection switch by means of which it is, for example, possible to generate infrared radiation only. This variant is not shown in FIG. 1.

The timer circuit for the discharge tube 4 will now be described. This timer circuit consists of a resistor-capacitor circuit. The capacitor is indicated by 10. A number of resistors 11 to 21 inclusive can be selectively arranged in series with the capacitor 10. These resistors are divided into two groups. The first group comprises the resistors 11 to 14 inclusive and the second group the resistors 15 to 21 inclusive. The resistors 11 to 14 inclusive are used to adjust the timer circuit to a certain skin sensitivity of the person to be irradiated by the discharge tube 4. The resistors 15 to 21 inclusive are used to perform a given radiation treatment by the relevant person. Further particulars concerning the circuit of the resistors 11 to 21 inclusive are found in U.S. Pat. No. 3,909,659. The resistors of the first group 11 to 14 inclusive, and those of the second group 15 to 21 inclusive, can be selectively interconnected by means of two switches 22 and 23 respectively. The timer circuit is fed via terminal 1, a tapping point 25, a resistor 26 and a diode 27. A further diode 28 is connected to a junction between the resistor 26 and the diode 27. The other side of the diode 28 is connected to a main electrode of the tube 4. Further particulars about the compensating action of the diodes 27 and 28 on the radiation period can also be found in the above-mentioned U.S. Patent.

The resistor 15 is connected to the capacitor 10. The other side of this capacitor is connected to a measuring resistor 30. The other side of the measuring resistor 30 is connected to a resistor 31. The other side of the resistor 31 is connected to a contact 32 of a switch 33 which is mechanically coupled to the switch 6. A contact of the switch 33 is connected to the input terminal 2. The portion of the time circuit described above is the resistor-capacitor (RC) circuit. The following describes that portion of the timer circuit which, in the case of a properly operating timer circuit, is used for switching off the discharge tube 4 via the switch 6.

A junction between resistor 15 and the capacitor 10 is connected to a control electrode of a (second) field effect transistor 35. The drain electrode (D) of this transistor 35 is connected to the base of an auxiliary transistor 36, which is of the pnp-type. The source electrode (S) of the transistor 35 is connected to the collector of the transistor 36. The emitter-base junction of the transistor 36 is furthermore shunted by a resistor 37. The emitter of the transistor 36 is connected to a first end 40 of an energizing winding of a relay which operates the coupled switches 33 and 6. The collector of the transistor 36 is connected to the other end 41 of said energizing winding. The energizing winding receives current during the irradiation via input terminal 1, tap 25, a diode 45, a resistor 46, a resistor 47, winding 40, 41, and a zener diode 42 to the input terminal 2.

Now follows a description of a safety circuit for this irradiation apparatus. This circuit is made operative when the current through the capacitor 10—during irradiation with the discharge tube 4—is too low. This safety circuit comprises inter alia a (first) field effect transistor 50. The control electrode of the transistor 50 is connected to a junction betwween the capacitor 10 and the measuring resistor 30. The D-electrode of the field effect transistor 50 is connected to the base of an auxiliary transistor 51 of the npn-type. The S-electrode of the field effect transistor 50 is connected to the emitter of the transistor 51. The main electrode circuit of the transistor 51 shunts the energizing winding which is situated between the points 40 and 41.

Finally some through-connections and further circuit components are indicated. Namely: the series arrangement of the resistors 11 to 14 inclusive is shunted by a capacitor 60. A junction between the capacitor 60 and the resistor 14 is connected via a conductor 61 to terminal 2. In addition, a junction between the resistor 15 and the capacitor 10 is also connected, via a conductor 62, to the switch 33. Furthermore a tapping point between the resistors 46 and 47 is connected on the one hand via a resistor 65 to the base of the transistor 51 and on the other hand to an electrode of a capacitor 66. The other side of the capacitor 66 is connected to the conductor 61. Finally, the collector of the transistor 36 is connected via a resistor 67 to the resistor 31. It should also be noted that the control electrode of the first field effect transistor 50 is connected via a capacitor 70 to the S-electrode of this field effect transistor. A diode 71 shunts the measuring resistor 30.

Now follows a description of the operation of this circuit. If the terminals 1 and 2 are connected to the above-mentioned a.c. voltage source, the switches 33 and 6 are initially in the left-hand position. This is the position not shown in FIG. 1. This means that no current flows as yet through the discharge tube 4. The situation in which the switch 33 is in the left-hand position results in that an initial charge is applied to the capacitor 10—via the diode 71—which is approximately equal to the zener voltage of the zener diode 42. In a practical embodiment this initial charge is, for example, approximately 15 Volts. The potential of the lower electrode of the capacitor is positive relative to that of the upper electrode. The lower electrode of the capacitor 10 must be understood to mean that electrode of the capacitor 10 which is connected to the transistor 50.

Thereafter the switches 33 and 6 are moved to the right-hand position by manually operating a starting button K. Current then starts through the discharge tube 4 via the resistor 3 and the irradiation starts. Also the capacitor 10 of the timer circuit then starts carrying current via the two groups of resistors. In view of the direction of orientation of the diode 27 this is a current which causes a reduction of the initial charge of the capacitor 10, i.e., the capacitor discharges. In this situation the transistors 35 and 36 are cut-off. However, the transistor 50 is conducting, and consequently, the transistor 51 is cut-off. The two field effect transistors 35 and 50 are of a type which is non-conducting if the control electrode has a potential relative to the S-electrode which is lower than minus 0.7 Volt on the average, on the average, and which is conducting if the control electrode has a higher potential.

If the timer circuit now operates properly, the second field effect transistor 35 will begin to conduct when if the potential of the upper electrode of the capacitor 10 exceeds the minus 0.7 Volt relative to the S-electrode of the transistor 35. The transistor 36 then also becomes conducting and this results in a short-circuiting of the energizing winding between the points 40 and 41 of the relay switch 6. Consequently, the switch 6 is again moved to its left-hand position. This terminates the current flow through the discharge tube 4.

If now, however, owing to an additional contact resistance, or a loose contact, the current strength through the capacitor 10 is below normal, such a difference in potential will be produced via the measuring resistor 30 between the control electrode and the S-electrode of the first field effect transistor 50—owing to the small voltage drop across the measuring resistor 30—that this transistor 50 is cut-off. This causes the auxiliary transistor 51 to become conducting, with the result that the energizing winding passes no current between the points 40 and 41, so that the contact 6 again moves to the left-hand position. As a result the discharge tube 4 is switched off.

A further case of an interference occurs if the capacitor 10 becomes short-circuited due to a fault. It is clear that it is then not possible to give this capacitor 10 an initial charge. Consequently, at the moment one wants to start the actual radiation, this radiation is immediately ended via the second field effect transistor 35 and the transistor 36.

The resistor 67 together with the resistor 31 constitutes a voltage divider for adjusting the circuit of the first field effect transistor 50.

Capacitor 70 is used for preventing an unintentional switching off of the sun lamp in the case of a brief rapid voltage change in the circuit. The capacitors 60 and 66 are used for smoothing the single-phase rectified supply voltages. The potential at the base of the transistor 51 is fixed by means of the resistor 65 and also the control by means of the field effect transistor 50 is enabled by this resistor.

Besides the advantage that this irradiation apparatus is rapidly switched-off in the case of a defect in the timer circuit, an additional advantage of this apparatus according to the invention is that only one main capacitor 10 is required. By means of that sole capacitor the timer circuit and also the safety circuit can function properly. The preparative process as regards the initial charge of the capacitor 10 prevents a defect in this capacitor from going unnoticed.

In a practical embodiment the circuit components have, for example, the following nominal values:

resistor 11 169 k Ω
resistor 12 31 k Ω
resistor 13 20 k Ω
resistor 14 110 k Ω
resistor 15 11 M Ω
resistor 16 6.2 M Ω
resistor 17 8.2 M Ω
resistor 18 8.2 M Ω
resistor 19 12 M Ω
resistor 20 13 M Ω
resistor 21 13 M Ω
resistor 26 412 k Ω
resistor 37 1 k Ω
resistor 46 15 k Ω
resistor 47 470 k Ω
measuring resistor 68 M Ω
capacitor 10 3.3 μFarad
capacitor 60 0.33 μFarad
capacitor 66 47 nanoFarad.

In this embodiment the threshold value of the current through capacitor 10 is approximately 50 nanoAmperes.

In FIG. 2 the difference in potential $V_1$, between the upper electrode of the capacitor and the S-electrode of the field effect transistor 35 is plotted, by way of example, versus time t during the period of time discharge tube 4 emits radiation.

In FIG. 2 the difference in potential $V_2$ between the lower electrode of the capacitor 10 and the S-electrode of the field effect transistor 50 is also plotted versus time t during the period of time discharge tube 4 emits radiation.

It should be noted that there is substantially no difference in potential between the S-electrodes of the two field effect transistors 35 and 50 in the circuit of FIG. 1.

Also plotted versus time t is, for that example, in the current i through the capacitor 10 during radiation. The switch-on waveform of this capacitor current is not shown.

Dashes ($V_1'$, $V_2'$ and i') indicate an interference situation in which the capacitor current i' is too low. In FIG. 2 the time t is expressed in minutes (m).

Normally the sun lamp, i.e., the discharge tube 4 (see FIG. 1), should only be on in the case of the above examples between the instant S (=start) and the instant B (see FIG. 2). Owing to the inteference—without the use of the invention—the radiation would not finish until, for example, the instant E. By using the invention switch-off already takes place at the instant D because the $V_2'$ potential then becomes too low to keep the first field effect transistor 50 (see FIG. 1) in its conducting state. As a result that the auxiliary transistor 51 then becomes conducting and the discharge tube 4 is switched off via the energizing winding and switch 6.

This considerably reduces the chance of an excessive radiation dose on the object in the case of a defect in the timer circuit.

What is claimed is:

1. An irradiation apparatus comprising a pair of input terminals for coupling the apparatus to a source of supply voltage, an electric discharge tube, a timing circuit including a capacitor for automatically reducing, by means of an auxiliary device, the tube irradiation after a predetermined irradiation period, means for coupling the discharge tube, the timing circuit and the auxiliary device to said input terminals, and a safety circuit coupled to said capacitor and to said auxiliary device so as to reduce the tube irradiation in the case of a defect in the timing circuit, said safety circuit comprising a circuit impedance element connected in series with the capacitor so that the capacitor current flows through the impedance element during an irradiation period, and means coupled to the impedance element and the auxiliary device for monitoring the flow of capacitor current so as to trigger the auxiliary device to reduce the tube irradiation if the capacitor current falls below a threshold level indicative of a defect in the timing circuit.

2. An irradiation apparatus as claimed in claim 1 wherein said coupling means includes a relay contact connected in series with the discharge tube across said input terminals, and the auxiliary device includes an energizing device for control of the relay contact and connected in circuit so that a capacitor current below the threshold value opens the relay contact via the energizing device.

3. An irradiation apparatus as claimed in claim 2 wherein the circuit element in series with the capacitor comprises a measuring resistor.

4. An irradiation apparatus as claimed in claim 3 wherein the current monitoring means comprises a first field effect transistor having an input circuit connected to the measuring resistor so that the measuring resistor voltage drop controls the operation of the first field effect transistor.

5. An irradiation apparatus as claimed in claim 4, characterized in that the first field effect transistor is a part of a control circuit of a first auxiliary transistor, and means connecting the main electrode circuit of said first auxiliarly transistor in shunt with the energizing device for the relay contact, the relay contact being a make-contact.

6. An irradiation apparatus as claimed in claim 5 characterized in that the electrode of the capacitor remote from the measuring resistor is connected to a control electrode of a second field effect transistor forming part of the timing circuit.

7. An irradiation apparatus as claimed in claim 6, characterized in that the second field effect transistor is part of a control circuit of a second auxiliary transistor wherein the main electrode circuit of the second auxiliary transistor also shunts the energizing device for the relay contact.

8. An irradiation apparatus as claimed in claim 1 further comprising means for providing the capacitor, prior to irradiation, with an initial voltage of a polarity such that said capacitor current is the discharge current of the capacitor.

9. An irradiation apparatus as claimed in claim 8, characterized in that the means for providing the initial voltage comprises a change-over switch coupled to the capacitor and a zener diode.

10. An irradiation apparatus as claimed in claim 1 wherein said coupling means includes a switching device controlled by said auxiliary device and connected in series with said circuit impedance element and the capacitor across said input terminals, said apparatus further comprising a diode coupling the capacitor to the input terminals via said switching device so as to provide a unidirectional charge path for charging the capacitor to a predetemined voltage level prior to the start of an irradiation period.

11. An irradiation apparatus as claimed in claim 1 wherein the current monitoring means comprises a first transistor having an input circuit coupled to the circuit impedance element and an output circuit coupled to a control input of the auxiliary device.

12. An irradiation apparatus as claimed in claim 11 wherein the timing circuit includes a second transistor having a control electrode coupled to the capacitor and an output electrode coupled to a control input of the auxiliary device.

13. An irradiation apparatus as claimed in claim 12 wherein the auxiliary device comprises, means for controlling the supply of an energizing voltage to the discharge tube, first and second auxiliary transistors having control electrodes respectively connected to the output electrodes of said first and second transistors, and means connecting said first and second auxiliary transistors in parallel to said energizing voltage controlling means.

14. An irradiation apparatus as claimed in claim 1 wherein the circuit element in series with the capacitor comprises a measuring resistor.

15. An irradiation apparatus as claimed in claim 14 wherein the current monitoring means comprises a first field effect transistor having an input circuit connected to the measuring resistor so that the measuring resistor voltage drop controls the operation of the first field effect transistor.

* * * * *